United States Patent [19]
Kamegawa

[11] Patent Number: 6,094,259
[45] Date of Patent: Jul. 25, 2000

[54] OPTICAL EXTENSOMETER AND REFERENCE LINE MARK THEREFOR

[75] Inventor: Masayuki Kamegawa, Nara, Japan

[73] Assignee: Shimadzy Corporation, Kyoto, Japan

[21] Appl. No.: 09/222,761

[22] Filed: Dec. 30, 1998

[51] Int. Cl.$^7$ ..................................................... G01N 3/08
[52] U.S. Cl. ............................................. 356/32; 73/800
[58] Field of Search ........................... 356/32, 401, 375; 73/800, 788

[56] References Cited

U.S. PATENT DOCUMENTS

| | | | |
|---|---|---|---|
| 4,690,001 | 9/1987 | Harvey et al. | 73/800 |
| 4,841,779 | 6/1989 | Mitsuhashi et al. | 73/826 |
| 4,880,309 | 11/1989 | Wanta | 356/401 |
| 5,568,259 | 10/1996 | Kamegawa | 73/800 |
| 5,827,629 | 11/1998 | Miyatake | 356/401 |

*Primary Examiner*—Richard A. Rosenberger
*Attorney, Agent, or Firm*—Kanesaka & Takeuchi

[57] ABSTRACT

A reference line mark for an optical extensometer of the invention has a mark main body with a boundary shape, in which a reflectance of light is different from other portions. The boundary shape is arranged such that when the mark main body is integrated in a direction perpendicular to the deformation direction under the condition that the mark is attached to a test piece, results of the integration constitute an isosceles triangle having a base in a deformation direction of the test piece. Thus, data points for obtaining edge portions of the mark can be increased, and error-free approximation can be available. Elongation of the test piece can be measured with high accuracy at high computing speed.

7 Claims, 3 Drawing Sheets

FIG. 1(a)
FIG. 1(b)
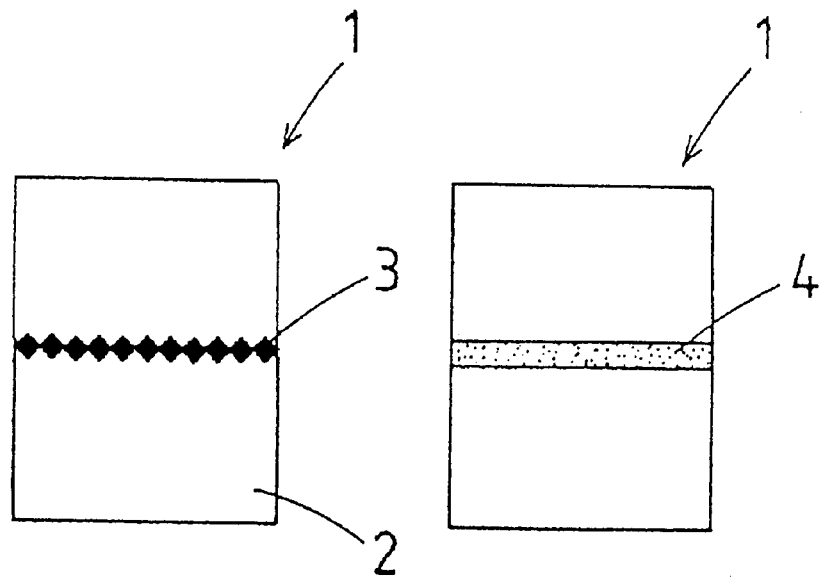
FIG. 2
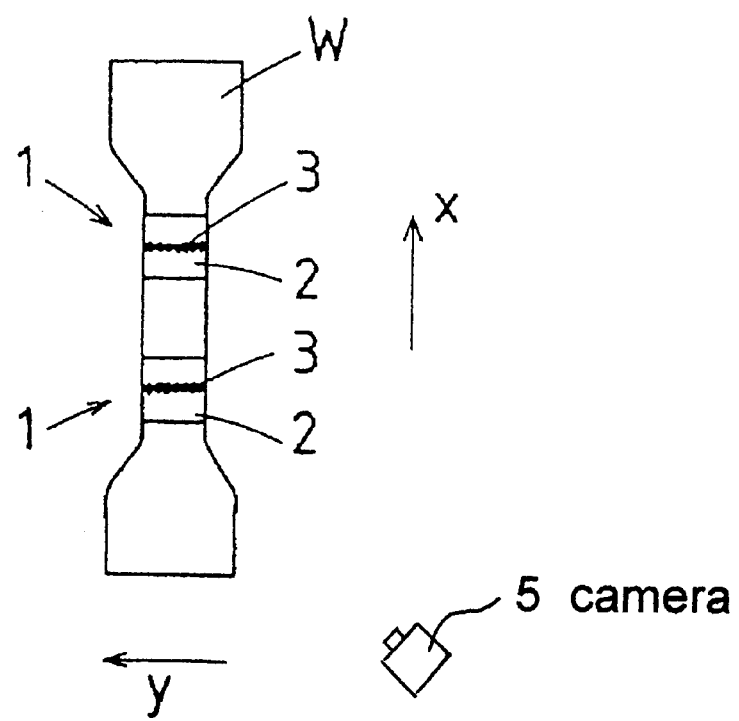

reference line mark

OPTICAL EXTENSOMETER AND REFERENCE LINE MARK THEREFOR

BACKGROUND OF THE INVENTION AND RELATED STATEMENT

The present invention relates to an optical extensometer, and a reference line mark therefor, and more particularly to a mark provided at a reference line in a test piece in order to discern the position of the reference line in case an elongation between the reference lines is measured by using image data obtained by photographing the test piece by a camera.

For example, as an extensometer for measuring, without contacting, an elongation occurred when a tensile load is applied to a test piece by a material testing machine, there has been known a so-called optical extensometer using photograph signals for the test piece by a camera.

In the optical extensometer, in order to discern respective reference line positions on the test piece from the photograph signal by the camera, marks are provided at the respective reference line positions. Normally, the reference line marks are directly printed or drawn on a front surface of the test piece, or a sticker on which the reference line mark is printed is adhered at a pertinent position on the test piece. Also, in order to make a clear difference of contrast in a picture signal from the camera, for example, in case of the sticker, the mark is applied in black on a white ground, or white on a black ground such that the reflectance relative to the back ground is extremely different from each other. And, in case the mark is directly printed on the front surface of the test piece, the mark is provided by a color having reflectance which is different from reflectance of the front surface of the test piece.

Conventionally, as shown in FIG. 5, the reference line marks as described above are located at positions corresponding to the respective reference lines, and include simple straight lines extending in a direction y perpendicular to a deformation (elongation) direction x of a test piece W.

In the optical extensometer as described above, generally, in order to specify the respective reference line positions based on the photograph signal of the test piece from the camera, the following operations are carried out. Each picture element or pixel data is integrated in the direction (y direction in FIG. 5) perpendicular to the deformation (elongation) direction of the test piece to obtain a profile P(x) of a shade in the elongation direction (x direction) of the test piece as shown in FIG. 6. An increasing point and a decreasing point of the profile P(x), i.e. x direction coordinates of intersections between the profile P(x) and a threshold level Th, are calculated to obtain, for example, a center position therebetween as a reference line position. Incidentally, L designates a pitch of the picture element in the figure.

Also, in case of obtaining a resolution greater than that of the picture element or pixel of the camera, an interpolation operation of the aforementioned profile P(x) is required. In order to achieve the first degree in JIS (Japanese Industrial Standards), i.e. less than 3 $\mu$m or 1% of the elongation in precision, an interpolation operation with high accuracy is indispensable. Here, in this interpolation operation, practically, it is effective to lower the degree in the approximate formula so as to accelerate computing speed, and in case of approximating by a linear equation which has the fastest computing speed, the increasing point A and the decreasing point B are calculated by the following equations.

$$A = x_i + \frac{Th - P(x_i)}{P(x_{i+1}) - P(x_i)}$$

$$B = x_j + \frac{P(x_j) - Th}{P(x_j) - P(x_{j+1})}$$

Equations 1

In this case, however, there is a problem that an error in the computation is influenced by a shape of the profile. The error tends to become 0 when a true edge is located on a center of the picture element, and tends to become maximum when the true edge is located away from the center of the picture element with a distance of a half size of the picture element. For example, if the pitch of the picture element is 0.1 mm, there can be seen a phenomenon that the position of the mark as a result of computation is meandered in a cyclic movement of 0.1 mm as shown in FIG. 7. As a result, measured results for the elongation are meandered, and especially, meandering in a proportional elastic area of a material results in deteriorating an accuracy of computing an elastic modulus.

Incidentally, although the shape of the profile greatly depends on adjustments of focus and contrast, if the focus is optimally adjusted and contrast is toned up, a meandering degree is increased on the contrary.

The present invention has been made in view of the aforementioned problems, and an object of the present invention is to provide a reference line mark for an optical extensometer, wherein a reference line position with high accuracy can be always specified by an interpolation computation using a linear equation which is the most advantageous in view of the computing speed, so that an elongation with high accuracy can be measured at high speed.

Another object of the invention is to provide an optical extensometer formed of the reference line mark and a camera for providing photograph signals of the test piece with the mark main body.

Further objects and advantages of the invention will be apparent from the following description of the invention.

SUMMARY OF THE INVENTION

To achieve the above object, the present invention provides a reference line mark for an optical extensometer, wherein a boundary shape for an area, in which a reflectance of light is different from other portions, is formed such that a function, which is obtained by integrating the boundary shape in a direction (y direction) perpendicularly to a deformation direction (x direction) of a test piece under a condition that the reference line mark is attached to the test piece, constitutes an isosceles triangle having a base in the deformation direction (x direction).

Here, in the present invention, as the boundary shape as described above, it is preferable to have a shape in which a plurality of diamond shapes is arranged side by side in the direction (y direction) perpendicular to the deformation direction of the test piece. Thus, when the reference line mark is attached, a position of a central line thereof can be accurately and sensuously perceived by eye sight.

Here, as embodiments of the reference line mark of the present invention, there can be made a sticker type on which the mark having the boundary shape as described above is printed or drawn in order to be adhered on a front surface of the test piece. The mark may be directly printed on the front surface of the test piece. Also, a sheet-type or plate-like mask with holes having the shape as described above may be made, by which the mark is directly drawn or painted by a spray on the front surface of the test piece.

In the present invention, by inclining the edge portions, which extend in the y direction, of the profile as a result of integrating the photograph signal of the reference line mark in the y direction, data points provided for the interpolation computation for a function at the edge portions are increased, and straight lines of the edge portions are accurately calculated by the interpolation computation using a linear approximate formula which is the most advantageous in view of the computing speed. Thus, intersecting points between the edge portions and a threshold level Th can be always accurately found.

Namely, in case of using the conventional reference line mark in the form of a simple straight line, the profile obtained by integrating the mark in the y direction constitutes a shape having edge portions which extend substantially along the y direction as shown in FIG. 6, and an expansion thereof toward the x direction is small. Thus, in connection with the pitch of the picture element in the x direction, data points used in the interpolation computation for the edge portions are limited.

On the other hand, in case the edge portions of the profile are inclined with respect to the y axis so as to expand in the x direction as in the present invention (referring to FIGS. 3 and 4), even if the picture element L in the x direction is the same as in the conventional mark, the data points used in the interpolation computation for the edge portions are increased, so that the straight lines at the edge portions can be accurately found. The profile after integrating in the y direction is made into an isosceles triangle, so that both increasing and decreasing points of edges can be accurately found, resulting in that a center of the reference line mark can be precisely specified.

Also, as a contour of the actual reference line mark, in order to obtain the profile in the shape of the isosceles triangle as described above, if a plurality of diamond shapes is arranged in the y direction, i.e. in the direction perpendicular to the deforming direction of the test piece, a center line of the mark can be accurately perceived by eye sight, resulting in facilitating the work for attaching the mark.

In the invention, an optical extensometer may be formed of the reference line mark and a camera for providing photograph signals of the test piece with the mark main body.

BRIEF DESCRIPTION OF THE DRAWINGS

FIG. 1(a) is a front view showing one embodiment of the present invention;

FIG. 1(b) is a rear view showing the embodiment of the present invention;

FIG. 2 is a view showing a condition that the embodiment of the invention is adhered to a test piece;

DETAILED DESCRIPTION OF PREFERRED EMBODIMENTS

Figure 3:
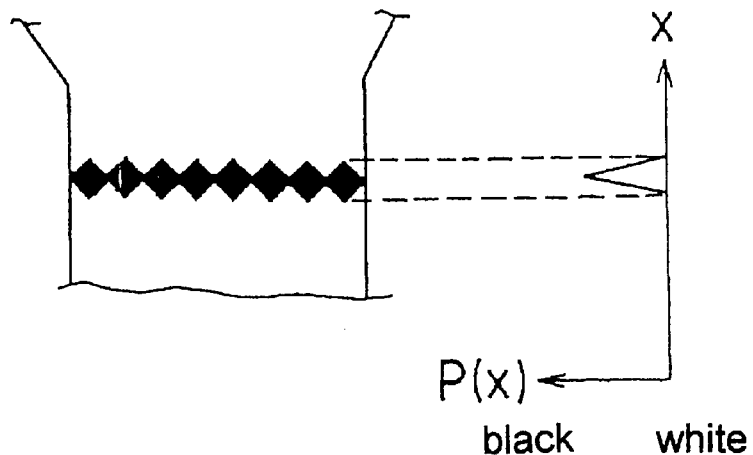
FIG. 3 is an explanatory view of a profile obtained when photograph signals by a camera in the present invention are integrated in a y direction.

Hereinafter, embodiments of the invention will be explained by referring to the drawings.

FIGS. 1(a) and 1(b) are explanatory views of an embodiment in which the present invention is applied in an sticker, wherein FIG. 1(a) is a front view thereof and FIG. 1(b) is a rear view thereof. Also, FIG. 2 is a view showing a condition that the embodiment of the invention is adhered to a test piece W.

A front surface of a sticker 1 is structured such that a ground 2 is white and a mark main body 3 is black, and on a rear surface side of the sticker 1, a glue 4 is provided only at a portion along the mark main body 3. Incidentally, it is preferable to make an area provided with the glue 4 to be narrow in width along the mark main body 3, so that the sticker 1 is not rotated easily with respect to a deformation of the test piece W in accordance with a progress of a test.

The mark main body 3 has a shape in which a plurality of diamond shapes is disposed side by side in a straight line. In this embodiment, each diamond shape is a square, and the diamond shapes are disposed such that respective diagonal lines thereof are arranged side by side in a straight line. Also, each diagonal line has a length of about 1 mm.

As shown in FIG. 2, the sticker as described above is adhered to the test piece W by the glue 4 provided on the rear surface of the sticker such that the mark main body 3 is placed along a reference line extending in a direction (y direction) perpendicular to an elongation direction (x direction) of the test piece W.

The test piece W with the reference line mark as described above is photographed by a camera 5, and when shading data of each picture element in the vicinity of the reference line mark is integrated in the y direction perpendicular to the elongation, more specifically, when the shading data of each picture element is integrated per row extending along the y axis, the profile P(x) constitutes an isosceles triangle having a base in the x direction as the elongation direction as shown in FIG. 3.

Figure 4:
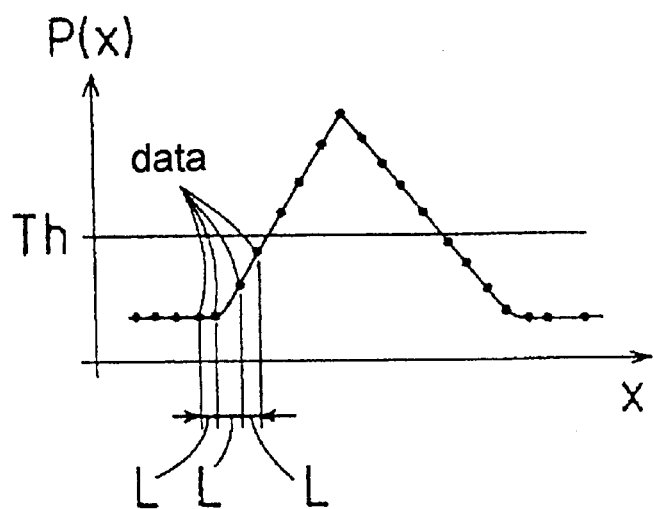
FIG. 4 is an explanatory view of data points which can be used in the interpolation computation for seeking edges of the profile obtained by integrating the photograph signals in the present invention.
Figure 5:
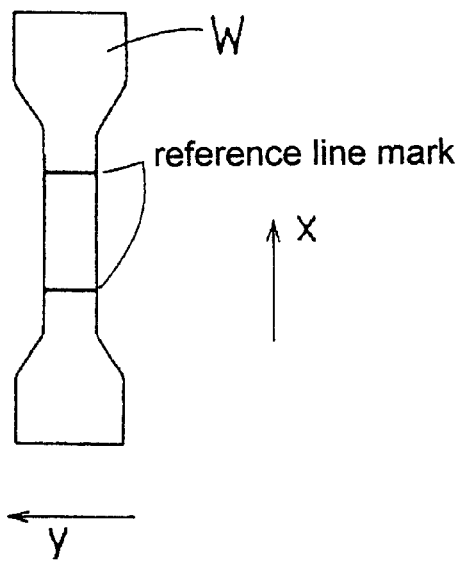
FIG. 5 is an explanatory view of a conventional reference line mark used in case an elongation of a test piece is measured by an optical extensometer.
Figure 6:
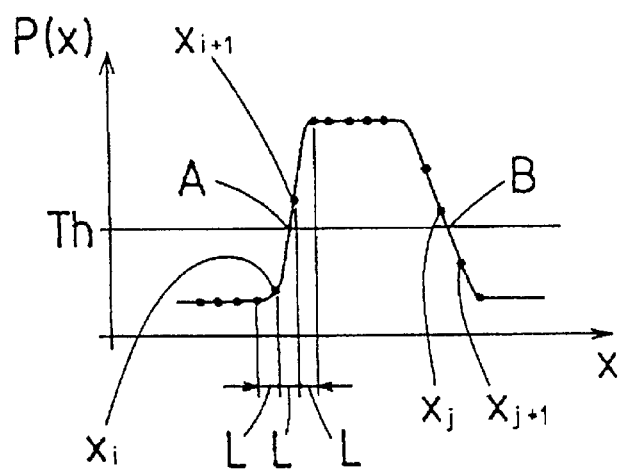
FIG. 6 is a an explanatory view showing a profile obtained by integrating photograph signals of the conventional reference line mark shown in FIG. 5 in a direction perpendicular to an elongation direction of the test piece.
Figure 7:
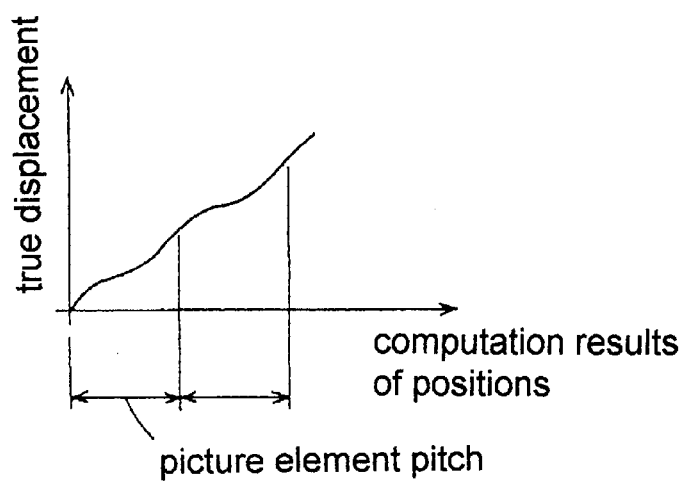
FIG. 7 an explanatory view showing a meandering line appeared in computation results of mark positions in case the conventional reference line mark is used.

In the profile as described above, both edge portions are inclined not perpendicularly to the x axis, so as to have a predetermined expansion in the x direction. Thus, in case of executing the interpolation computation in which a straight line of the edge portion is approximated by a linear equation, as shown in FIG. 4, in regard to the picture element pitch L in the x direction, the data points provided for the interpolation computation are extremely increased as compared to the conventional profile shown in FIG. 6. Accordingly, an accurate approximate formula which does not substantially cause an error can be obtained.

Also, a notable point in the aforementioned embodiment is that the elongation direction of the mark main body 3, that is, the direction of the reference line can be clearly perceived by an eye sight. Namely, although the mark may have another shape for obtaining the profile in a shape of an isosceles triangle having a base in an x direction as described above, the shape with a plurality of diamond shapes arranged in a straight line is extremely easy in perceiving the elongation direction of the mark as in a straight line, so that work for providing the mark can be facilitated.

Incidentally, although the mark main body 3 is black and the ground 2 is white in the above described embodiment, it is needless to say that a white mark main body can be provided on a black ground.

Also, other than the sticker adhered on the test piece as described above, the reference line mark of the present invention can be directly printed or drawn on the surface of the test piece. In case the mark is drawn, it is possible to use a mask in which holes are punched in the shape of the mark main body 3 as described above, so that the reference line mark can be drawn on the front surface of the test piece by a spray paint or the like through the mask.

The mark may be formed of a plurality of triangular shapes, i.e. isosceles triangle, arranged in a straight line in one direction, instead of the diamond shape.

As described above, according to the present invention, the boundary shape for an area in which a reflectance of light is different from other portions, that is, the contour of the mark, is formed such that the function, which is obtained by integrating the boundary shape in the y direction perpendicular to the deformation or elongating direction (x direction) of the test piece under the condition that the reference line mark is attached to the test piece, constitutes the isosceles triangle having the base in the x direction. Thus, both edge portions of the profile constitute oblique lines expanding in the x direction. Therefore, the data points which can be used for approximating the straight lines for the edge portions by interpolation are increased, so that the accurate approximate equation with few error can be always obtained and the edge position can be grasped with high accuracy. As a result, even if the conventional optical extensometer is used, an elongation can be measured accurately.

Also, as the actual shape of the mark for obtaining the profile as described above, if the shape in which a plurality of diamond shapes is aligned in a straight line is used, the reference line position can be easily perceived by eye sight as in the conventional mark in the form of the straight line.

While the invention has been explained with reference to the specific embodiments of the invention, the explanation is illustrative and the invention is limited only by the appended claims.

What is claimed is:

1. A reference line mark for an optical extensometer to be provided on a test piece, comprising:
    a mark main body provided on a reference line of a test piece and having an area in which a reflectance of light is different from a portion outside the area and boundary shape for defining the area, said boundary shape being arranged such that a function obtained by integrating the boundary shape in a direction perpendicular to a deformation direction of the test piece under a condition that the mark is attached to the test piece constitutes an isosceles triangle having a base in the deformation direction.

2. A reference line mark for an optical extensometer according to claim 1, wherein the mark main body is formed of a plurality of diamond shapes aligned in the direction perpendicular to the deformation direction.

3. A reference line mark for an optical extensometer according to claim 1, wherein said boundary shape of the mark main body includes on each side thereof a plurality of sharp points in the deformation direction.

4. A reference line mark for an optical extensometer according to claim 3, further comprising a ground outside the mark main body, said ground providing a sharp contrast relative to the area of the mark main body.

5. A reference line mark for an optical extensometer according to claim 4, wherein the mark main body is provided on each of two reference lines on the test piece so that an elongation between the two reference lines is measured from an image data obtained by photographing the test piece by a camera.

6. A reference line mark for an optical extensometer according to claim 3, wherein the mark main body and the ground are formed on a sheet with an adhesive on a surface opposite to the ground.

7. An optical extensometer comprising:
    a mark main body provided on a reference line of a test piece and having an area in which a reflectance of light is different from a portion outside the area and boundary shape for defining the area, said boundary shape being arranged such that a function obtained by integrating the boundary shape in a direction perpendicular to a deformation direction of the test piece under a condition that the mark is attached to the test piece constitutes an isosceles triangle having a base in the deformation direction, and
    a camera for providing photograph signals of the test piece with the mark main body.

* * * * *

UNITED STATES PATENT AND TRADEMARK OFFICE
CERTIFICATE OF CORRECTION

PATENT NO : 6,094,259
DATED : July 25, 2000
INVENTOR(S): Masayuki Kamegawa

It is certified that error appears in the above-identified patent and that said Letters Patent are hereby corrected as shown below:

Cover page, section [73]Assignee, change "Shimadzy Corporation" to --Shimadzu Corporation--.

Signed and Sealed this

Tenth Day of April, 2001

Attest:

NICHOLAS P. GODICI

Attesting Officer     Acting Director of the United States Patent and Trademark Office